US008945167B2

(12) United States Patent
Cole et al.

(10) Patent No.: US 8,945,167 B2
(45) Date of Patent: Feb. 3, 2015

(54) GASTRIC SPACE OCCUPIER SYSTEMS AND METHODS OF USE

(75) Inventors: David Cole, San Mateo, CA (US); Samuel T. Crews, Woodside, CA (US); Bretton Swope, Gaithersburg, MD (US); Andrew Smith, San Francisco, CA (US); John Lunsford, San Carlos, CA (US); Daniel J. Balbierz, Redwood City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/224,233

(22) Filed: Sep. 1, 2011

(65) Prior Publication Data
US 2011/0319924 A1 Dec. 29, 2011

Related U.S. Application Data

(62) Division of application No. 12/270,607, filed on Nov. 13, 2008, now abandoned.

(60) Provisional application No. 61/018,405, filed on Dec. 31, 2007.

(51) Int. Cl.
*A61M 29/00* (2006.01)
*A61F 5/00* (2006.01)

(52) U.S. Cl.
CPC .................................. *A61F 5/0036* (2013.01)
USPC ........................................................ 606/192

(58) Field of Classification Search
USPC .................. 606/191, 192, 198, 37; 600/37; 623/23.65
See application file for complete search history.

(56) References Cited

U.S. PATENT DOCUMENTS

| 1,408,865 A | 3/1922 | Codwell |
| 3,663,965 A | 5/1972 | Lee et al. |

(Continued)

FOREIGN PATENT DOCUMENTS

| CH | 680263 A5 | 7/1992 |
| EP | 0775471 | 5/1997 |

(Continued)

OTHER PUBLICATIONS

Rhode, "water tubes" [online] Amazon.com corporation, Mar. 4, 2006. [retrieved on Aug. 21, 2013] retrieved from the internet: <URL: http://www.amazon.com/WATER-TUBES/dp/B00B1GFBZG/ref=sr_1_25?ie=UTF8&qid=1377518592&sr=8-25&keywords=water+tubes>.*

(Continued)

*Primary Examiner* — Katherine Dowe
*Assistant Examiner* — Amy Shipley
(74) *Attorney, Agent, or Firm* — Bookoff McAndrews PLLC

(57) ABSTRACT

Systems for controlling obesity utilize a number of space occupiers positioned in the stomach to reduce the effective volume of the stomach. Such arrangements provides sufficient stomach volume consumption to induce weight loss, but enable use of space occupiers that are proportioned to minimize the threat of obstruction even if they should migrate into the intestine. In general, numerous small volume space occupiers are placed in the stomach such that the total volume equals or exceeds the single volume of prior art single unit space occupiers. However, each individual space occupier is proportioned so that it will pass without obstruction if it moves into the intestine.

13 Claims, 4 Drawing Sheets

(56) References Cited

U.S. PATENT DOCUMENTS

| | | | |
|---|---|---|---|
| 4,134,405 A | 1/1979 | Smit | |
| 4,207,890 A | 6/1980 | Mamajek et al. | |
| 4,246,893 A | 1/1981 | Berson | |
| 4,315,509 A | 2/1982 | Smit | |
| 4,331,277 A | 5/1982 | Green | |
| 4,403,604 A | 9/1983 | Wilkinson et al. | |
| 4,416,267 A | 11/1983 | Garren et al. | |
| 4,417,360 A | 11/1983 | Moasser | |
| 4,441,215 A | 4/1984 | Kaster | |
| 4,467,804 A | 8/1984 | Hardy et al. | |
| 4,485,805 A | 12/1984 | Foster, Jr. | |
| 4,501,264 A | 2/1985 | Rockey | |
| 4,607,618 A | 8/1986 | Angelchik | |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,739,758 A * | 4/1988 | Lai et al. | 606/1 |
| 4,747,849 A | 5/1988 | Galtier | |
| 4,846,836 A | 7/1989 | Reich | |
| 4,848,367 A | 7/1989 | Avant et al. | |
| 4,899,747 A | 2/1990 | Garren et al. | |
| 4,925,446 A | 5/1990 | Garay et al. | |
| 4,946,440 A | 8/1990 | Hall | |
| 4,969,896 A | 11/1990 | Shors | |
| 4,997,084 A | 3/1991 | Opie et al. | |
| 5,006,106 A | 4/1991 | Angelchik | |
| 5,037,021 A | 8/1991 | Mills et al. | |
| 5,061,275 A | 10/1991 | Wallsten et al. | |
| 5,084,061 A | 1/1992 | Gau et al. | |
| 5,088,979 A | 2/1992 | Filipi et al. | |
| 5,163,952 A | 11/1992 | Froix | |
| 5,211,658 A | 5/1993 | Clouse | |
| 5,234,454 A | 8/1993 | Bangs | |
| 5,246,456 A | 9/1993 | Wilkinson | |
| 5,259,399 A | 11/1993 | Brown | |
| 5,263,629 A | 11/1993 | Trumbull et al. | |
| 5,290,217 A | 3/1994 | Campos | |
| 5,306,300 A | 4/1994 | Berry | |
| 5,314,473 A | 5/1994 | Godin | |
| 5,327,914 A | 7/1994 | Shlain | |
| 5,345,949 A | 9/1994 | Shlain | |
| 5,355,897 A | 10/1994 | Pietrafitta et al. | |
| 5,401,241 A | 3/1995 | Delany | |
| 5,403,326 A | 4/1995 | Harrison et al. | |
| 5,405,377 A | 4/1995 | Cragg | |
| 5,431,673 A | 7/1995 | Summers et al. | |
| 5,486,187 A | 1/1996 | Schneck | |
| 5,514,176 A | 5/1996 | Bosley, Jr. | |
| 5,535,935 A | 7/1996 | Vidal et al. | |
| 5,542,949 A | 8/1996 | Yoon | |
| 5,562,239 A | 10/1996 | Boiarski et al. | |
| 5,571,116 A | 11/1996 | Bolanos et al. | |
| 5,577,654 A | 11/1996 | Bishop | |
| 5,593,434 A | 1/1997 | Williams | |
| 5,597,107 A | 1/1997 | Knodel et al. | |
| 5,609,624 A | 3/1997 | Kalis | |
| 5,628,786 A | 5/1997 | Banas et al. | |
| 5,630,539 A | 5/1997 | Plyley et al. | |
| 5,647,526 A | 7/1997 | Green et al. | |
| 5,653,743 A | 8/1997 | Martin | |
| 5,662,713 A | 9/1997 | Andersen et al. | |
| 5,673,841 A | 10/1997 | Schulze et al. | |
| 5,674,241 A | 10/1997 | Bley et al. | |
| 5,706,998 A | 1/1998 | Plyley et al. | |
| 5,709,657 A | 1/1998 | Zimmon | |
| 5,720,776 A | 2/1998 | Chuter et al. | |
| 5,730,748 A * | 3/1998 | Fogarty et al. | 606/159 |
| 5,749,918 A | 5/1998 | Hogendijk et al. | |
| 5,762,255 A | 6/1998 | Chrisman et al. | |
| 5,771,903 A | 6/1998 | Jakobsson | |
| 5,785,684 A | 7/1998 | Zimmon | |
| 5,792,119 A | 8/1998 | Marx | |
| 5,820,584 A | 10/1998 | Crabb | |
| 5,839,639 A | 11/1998 | Sauer et al. | |
| 5,848,964 A | 12/1998 | Samuels | |
| 5,853,417 A * | 12/1998 | Fogarty et al. | 606/159 |
| 5,855,311 A | 1/1999 | Hamblin et al. | |
| 5,855,601 A | 1/1999 | Bessler et al. | |
| 5,856,445 A | 1/1999 | Korsmeyer | |
| 5,861,036 A | 1/1999 | Godin | |
| 5,868,141 A | 2/1999 | Ellias | |
| 5,887,594 A | 3/1999 | LoCicero, III | |
| 5,897,562 A | 4/1999 | Bolanos et al. | |
| 5,899,913 A * | 5/1999 | Fogarty et al. | 606/159 |
| 5,910,144 A | 6/1999 | Hayashi et al. | |
| 5,922,019 A | 7/1999 | Hankh et al. | |
| 5,947,983 A | 9/1999 | Solar et al. | |
| 5,993,473 A | 11/1999 | Chan et al. | |
| 5,993,483 A | 11/1999 | Gianotti | |
| 6,016,848 A | 1/2000 | Egrees | |
| 6,051,015 A | 4/2000 | Maahs | |
| 6,068,639 A * | 5/2000 | Fogarty et al. | 606/159 |
| 6,086,600 A | 7/2000 | Kortenbach | |
| 6,098,629 A | 8/2000 | Johnson et al. | |
| 6,102,922 A | 8/2000 | Jakobsson et al. | |
| 6,113,609 A | 9/2000 | Adams | |
| 6,120,534 A | 9/2000 | Ruiz | |
| 6,146,416 A | 11/2000 | Andersen et al. | |
| 6,159,146 A | 12/2000 | El Gazayerli | |
| 6,159,238 A | 12/2000 | Killion et al. | |
| 6,197,022 B1 | 3/2001 | Baker | |
| 6,206,930 B1 | 3/2001 | Burg et al. | |
| 6,245,088 B1 | 6/2001 | Lowery | |
| 6,251,132 B1 | 6/2001 | Ravenscroft et al. | |
| 6,254,642 B1 | 7/2001 | Taylor | |
| 6,258,120 B1 | 7/2001 | McKenzie et al. | |
| 6,264,700 B1 | 7/2001 | Kilcoyne et al. | |
| 6,287,334 B1 | 9/2001 | Moll et al. | |
| 6,302,917 B1 | 10/2001 | Dua et al. | |
| 6,358,197 B1 | 3/2002 | Silverman et al. | |
| 6,416,522 B1 | 7/2002 | Strecker | |
| 6,425,916 B1 | 7/2002 | Garrison et al. | |
| 6,443,159 B1 * | 9/2002 | Fogarty et al. | 128/898 |
| 6,454,785 B2 | 9/2002 | De Hoyos Garza | |
| 6,460,543 B1 | 10/2002 | Forsell | |
| 6,461,366 B1 | 10/2002 | Seguin | |
| 6,494,888 B1 | 12/2002 | Laufer et al. | |
| 6,494,895 B2 | 12/2002 | Addis | |
| 6,503,264 B1 | 1/2003 | Birk | |
| 6,506,196 B1 | 1/2003 | Laufer et al. | |
| 6,527,784 B2 | 3/2003 | Adams et al. | |
| 6,527,787 B1 * | 3/2003 | Fogarty et al. | 606/159 |
| 6,540,789 B1 | 4/2003 | Silverman et al. | |
| 6,544,291 B2 | 4/2003 | Taylor | |
| 6,547,801 B1 | 4/2003 | Dargent et al. | |
| 6,558,400 B2 | 5/2003 | Deem et al. | |
| 6,558,429 B2 | 5/2003 | Taylor | |
| 6,572,627 B2 | 6/2003 | Gabbay | |
| 6,572,629 B2 | 6/2003 | Kalloo | |
| 6,575,896 B2 | 6/2003 | Silverman et al. | |
| 6,592,596 B1 | 7/2003 | Geitz et al. | |
| 6,596,023 B1 | 7/2003 | Nunez et al. | |
| 6,607,555 B2 | 8/2003 | Patterson et al. | |
| 6,627,206 B2 | 9/2003 | Lloyd | |
| 6,632,227 B2 | 10/2003 | Adams | |
| 6,663,639 B1 | 12/2003 | Laufer et al. | |
| 6,675,809 B2 | 1/2004 | Stack et al. | |
| 6,733,512 B2 | 5/2004 | McGhan | |
| 6,740,098 B2 | 5/2004 | Abrams et al. | |
| 6,740,121 B2 | 5/2004 | Geitz et al. | |
| 6,746,460 B2 | 6/2004 | Gannoe et al. | |
| 6,755,869 B2 | 6/2004 | Geitz | |
| 6,764,518 B2 | 7/2004 | Godin | |
| 6,773,440 B2 | 8/2004 | Gannoe et al. | |
| 6,773,441 B1 | 8/2004 | Laufer et al. | |
| 6,790,214 B2 | 9/2004 | Kraemer et al. | |
| 6,790,237 B2 | 9/2004 | Stinson | |
| 6,821,285 B2 | 11/2004 | Laufer et al. | |
| 6,835,200 B2 | 12/2004 | Laufer et al. | |
| 6,840,946 B2 * | 1/2005 | Fogarty et al. | 606/159 |
| 6,845,776 B2 | 1/2005 | Stack et al. | |
| 6,916,332 B2 | 7/2005 | Adams | |
| 6,932,838 B2 | 8/2005 | Schwartz et al. | |

(56) References Cited

U.S. PATENT DOCUMENTS

| | | | |
|---|---|---|---|
| 6,960,233 B1 | 11/2005 | Berg et al. | |
| 6,966,875 B1 | 11/2005 | Longobardi | |
| 6,981,978 B2 | 1/2006 | Gannoe | |
| 6,981,980 B2 | 1/2006 | Sampson et al. | |
| 6,994,715 B2 | 2/2006 | Gannoe et al. | |
| 7,011,094 B2 | 3/2006 | Rapackie et al. | |
| 7,020,531 B1 | 3/2006 | Colliu et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,056,305 B2 | 6/2006 | Alvarez | |
| 7,066,945 B2 | 6/2006 | Hashiba et al. | |
| 7,077,852 B2* | 7/2006 | Fogarty et al. | 606/159 |
| 7,083,629 B2 | 8/2006 | Weller et al. | |
| 7,090,699 B2 | 8/2006 | Geitz | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,112,186 B2 | 9/2006 | Shah | |
| 7,120,498 B2 | 10/2006 | Imran et al. | |
| 7,121,283 B2 | 10/2006 | Stack et al. | |
| 7,146,984 B2 | 12/2006 | Stack et al. | |
| 7,147,140 B2 | 12/2006 | Wukusick et al. | |
| 7,152,607 B2 | 12/2006 | Stack et al. | |
| 7,160,312 B2 | 1/2007 | Saadat et al. | |
| 7,172,613 B2 | 2/2007 | Wazne | |
| 7,175,638 B2 | 2/2007 | Gannoe et al. | |
| 7,175,660 B2 | 2/2007 | Cartledge et al. | |
| 7,211,114 B2 | 5/2007 | Bessler et | |
| 7,214,233 B2 | 5/2007 | Gannoe et al. | |
| 7,220,237 B2 | 5/2007 | Gannoe et al. | |
| 7,220,284 B2 | 5/2007 | Kagan et al. | |
| 7,223,277 B2 | 5/2007 | DeLegge | |
| 7,229,428 B2 | 6/2007 | Gannoe et al. | |
| 7,229,453 B2 | 6/2007 | Anderson et al. | |
| 7,255,675 B2 | 8/2007 | Gertner et al. | |
| 7,261,722 B2 | 8/2007 | McGuckin, Jr. et al. | |
| 7,288,101 B2 | 10/2007 | Deem et al. | |
| 7,306,614 B2 | 12/2007 | Weller et al. | |
| 7,315,509 B2 | 1/2008 | Jeong et al. | |
| 7,316,716 B2 | 1/2008 | Egan | |
| 7,320,696 B2* | 1/2008 | Gazi et al. | 606/192 |
| 7,326,207 B2 | 2/2008 | Edwards | |
| 7,335,210 B2 | 2/2008 | Smit | |
| 7,347,863 B2 | 3/2008 | Rothe et al. | |
| 7,347,875 B2 | 3/2008 | Levine et al. | |
| 7,354,454 B2 | 4/2008 | Stack et al. | |
| 7,399,304 B2 | 7/2008 | Gambale et al. | |
| 7,431,725 B2 | 10/2008 | Stack et al. | |
| 7,588,584 B2* | 9/2009 | Fogarty et al. | 606/190 |
| 7,699,863 B2 | 4/2010 | Marco et al. | |
| 8,075,582 B2* | 12/2011 | Lointier et al. | 606/192 |
| 8,216,268 B2* | 7/2012 | Haller et al. | 606/196 |
| 8,267,888 B2* | 9/2012 | Marco et al. | 604/104 |
| 2001/0011543 A1 | 8/2001 | Forsell | |
| 2001/0020189 A1 | 9/2001 | Taylor | |
| 2001/0020190 A1 | 9/2001 | Taylor | |
| 2001/0021796 A1 | 9/2001 | Silverman et al. | |
| 2001/0044595 A1 | 11/2001 | Reydel et al. | |
| 2002/0016607 A1* | 2/2002 | Bonadio et al. | 606/192 |
| 2002/0022851 A1 | 2/2002 | Kalloo et al. | |
| 2002/0055757 A1 | 5/2002 | Torre et al. | |
| 2002/0072761 A1 | 6/2002 | Abrams et al. | |
| 2002/0082621 A1 | 6/2002 | Schurr et al. | |
| 2002/0099439 A1 | 7/2002 | Schwartz et al. | |
| 2002/0183767 A1 | 12/2002 | Adams et al. | |
| 2002/0183768 A1 | 12/2002 | Deem et al. | |
| 2002/0188354 A1 | 12/2002 | Peghini | |
| 2003/0009236 A1 | 1/2003 | Godin | |
| 2003/0040804 A1 | 2/2003 | Stack et al. | |
| 2003/0040808 A1 | 2/2003 | Stack et al. | |
| 2003/0065359 A1 | 4/2003 | Weller et al. | |
| 2003/0093117 A1 | 5/2003 | Saadat | |
| 2003/0109892 A1 | 6/2003 | Deem et al. | |
| 2003/0120289 A1 | 6/2003 | McGuckin, Jr. et al. | |
| 2003/0158569 A1 | 8/2003 | Wazne | |
| 2003/0191476 A1 | 10/2003 | Smit | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2003/0208209 A1 | 11/2003 | Gambale et al. | |
| 2003/0208223 A1* | 11/2003 | Kleiner | 606/198 |
| 2003/0220660 A1 | 11/2003 | Kortenbach et al. | |
| 2004/0006351 A1 | 1/2004 | Gannoe et al. | |
| 2004/0024386 A1 | 2/2004 | Deem et al. | |
| 2004/0030347 A1 | 2/2004 | Gannoe et al. | |
| 2004/0044353 A1 | 3/2004 | Gannoe | |
| 2004/0044354 A1 | 3/2004 | Gannoe et al. | |
| 2004/0044357 A1 | 3/2004 | Gannoe et al. | |
| 2004/0044364 A1 | 3/2004 | DeVries et al. | |
| 2004/0082963 A1 | 4/2004 | Gannoe et al. | |
| 2004/0088023 A1 | 5/2004 | Imran et al. | |
| 2004/0092892 A1 | 5/2004 | Kagan et al. | |
| 2004/0092974 A1 | 5/2004 | Gannoe et al. | |
| 2004/0093091 A1 | 5/2004 | Gannoe et al. | |
| 2004/0098043 A1 | 5/2004 | Trout | |
| 2004/0107004 A1 | 6/2004 | Levine et al. | |
| 2004/0117031 A1 | 6/2004 | Stack et al. | |
| 2004/0133219 A1 | 7/2004 | Forsell | |
| 2004/0138761 A1 | 7/2004 | Stack et al. | |
| 2004/0143342 A1 | 7/2004 | Stack et al. | |
| 2004/0148034 A1 | 7/2004 | Kagan et al. | |
| 2004/0153167 A1 | 8/2004 | Stack et al. | |
| 2004/0158331 A1 | 8/2004 | Stack et al. | |
| 2004/0162568 A1 | 8/2004 | Saadat et al. | |
| 2004/0172141 A1 | 9/2004 | Stack et al. | |
| 2004/0172142 A1 | 9/2004 | Stack et al. | |
| 2004/0186502 A1 | 9/2004 | Sampson et al. | |
| 2004/0210243 A1 | 10/2004 | Gannoe et al. | |
| 2004/0215216 A1 | 10/2004 | Gannoe et al. | |
| 2004/0220682 A1 | 11/2004 | Levine et al. | |
| 2004/0225183 A1 | 11/2004 | Michlitsch et al. | |
| 2004/0225305 A1 | 11/2004 | Ewers et al. | |
| 2004/0236419 A1 | 11/2004 | Milo | |
| 2004/0243152 A1 | 12/2004 | Taylor et al. | |
| 2004/0243223 A1 | 12/2004 | Kraemer et al. | |
| 2004/0267378 A1 | 12/2004 | Gazi et al. | |
| 2005/0004430 A1 | 1/2005 | Lee et al. | |
| 2005/0004681 A1 | 1/2005 | Stack et al. | |
| 2005/0033326 A1 | 2/2005 | Briganti et al. | |
| 2005/0033345 A1 | 2/2005 | DeLegge | |
| 2005/0049718 A1 | 3/2005 | Dann et al. | |
| 2005/0075654 A1 | 4/2005 | Kelleher | |
| 2005/0080444 A1 | 4/2005 | Kraemer et al. | |
| 2005/0085787 A1 | 4/2005 | Laufer et al. | |
| 2005/0096673 A1 | 5/2005 | Stack et al. | |
| 2005/0096750 A1 | 5/2005 | Kagan et al. | |
| 2005/0149114 A1 | 7/2005 | Cartledge et al. | |
| 2005/0159769 A1 | 7/2005 | Alverdy | |
| 2005/0177181 A1 | 8/2005 | Kagan et al. | |
| 2005/0183732 A1 | 8/2005 | Edwards | |
| 2005/0192599 A1 | 9/2005 | Demarais | |
| 2005/0192615 A1 | 9/2005 | Torre et al. | |
| 2005/0216040 A1 | 9/2005 | Gertner et al. | |
| 2005/0216042 A1 | 9/2005 | Gertner | |
| 2005/0228504 A1* | 10/2005 | Demarais | 623/23.65 |
| 2005/0240279 A1 | 10/2005 | Kagan et al. | |
| 2005/0247320 A1 | 11/2005 | Stack et al. | |
| 2005/0250980 A1 | 11/2005 | Swanstrom et al. | |
| 2005/0251158 A1 | 11/2005 | Saadat et al. | |
| 2005/0251162 A1 | 11/2005 | Rothe et al. | |
| 2005/0256533 A1 | 11/2005 | Roth et al. | |
| 2005/0256587 A1 | 11/2005 | Egan | |
| 2005/0261712 A1 | 11/2005 | Balbierz et al. | |
| 2005/0267405 A1 | 12/2005 | Shah | |
| 2005/0267499 A1 | 12/2005 | Stack et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2005/0283107 A1 | 12/2005 | Kalanovic et al. | |
| 2006/0015006 A1 | 1/2006 | Laurence et al. | |
| 2006/0020278 A1 | 1/2006 | Burnett et al. | |
| 2006/0058829 A1 | 3/2006 | Sampson et al. | |

(56) References Cited

U.S. PATENT DOCUMENTS

| | | |
|---|---|---|
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1 | 8/2006 | Saadat et al. |
| 2006/0178691 A1 | 8/2006 | Binmoeller |
| 2006/0189840 A1* | 8/2006 | Walsh et al. .............. 600/16 |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276428 A1 | 11/2007 | Haller et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0097510 A1 | 4/2008 | Albrecht et al. |
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0269797 A1 | 10/2008 | Stack et al. |
| 2008/0319471 A1 | 12/2008 | Sosnowski et al. |
| 2009/0182424 A1 | 7/2009 | Marco et al. |

FOREIGN PATENT DOCUMENTS

| | | |
|---|---|---|
| EP | 1492478 | 1/2005 |
| EP | 1602336 | 12/2005 |
| FR | 2768324 | 3/1999 |
| JP | 09-168597 | 6/1997 |
| WO | WO 91/01117 | 2/1991 |
| WO | WO 97/47231 | 12/1997 |
| WO | WO 00/12027 | 3/2000 |
| WO | WO 00/32137 | 6/2000 |
| WO | WO 00/78227 | 12/2000 |
| WO | WO 01/41671 | 6/2001 |
| WO | WO 01/45485 | 6/2001 |
| WO | WO 01/49359 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 | 11/2003 |
| WO | WO 03/094785 | 11/2003 |
| WO | WO 03/099137 | 12/2003 |
| WO | WO 2004/019765 A2 | 3/2004 |
| WO | WO 2004/019787 | 3/2004 |
| WO | WO 2004/032760 | 4/2004 |
| WO | WO 2004/037064 | 5/2004 |
| WO | WO 2004/041133 | 5/2004 |
| WO | WO 2004/064685 | 8/2004 |
| WO | WO 2004/080336 | 9/2004 |
| WO | WO 2004/110285 | 12/2004 |
| WO | WO 2005/037152 | 5/2005 |
| WO | WO 2005/079673 | 9/2005 |
| WO | WO 2005/096991 | 10/2005 |
| WO | WO 2005/105003 | 11/2005 |
| WO | WO 2006/016894 | 2/2006 |
| WO | WO 2006/055365 | 5/2006 |
| WO | WO 200612759 | 11/2006 |
| WO | WO 2007/041598 | 4/2007 |
| WO | WO 2008/030403 | 3/2008 |
| WO | WO 2008/033409 | 3/2008 |
| WO | WO 2008/033474 | 3/2008 |
| WO | WO 2008/141288 | 11/2008 |
| WO | WO 2009/011881 | 1/2009 |
| WO | WO 2009/011882 | 1/2009 |
| WO | WO 2009/086549 | 7/2009 |
| WO | WO 2004/064680 | 8/2009 |
| WO | WO 2009/117533 | 9/2009 |
| WO | WO 2010/054399 | 5/2010 |
| WO | WO 2010/054404 | 5/2010 |

OTHER PUBLICATIONS

Ningbo, "water snake" [online] Amazon.com corporation [retrieved on Aug. 26, 2013] retrieved from the internet: <URL: http://www.amazon.com/NINGBO-CO-WTR-Water-Snake-long/dp/B001E4PVMS/ref=pd_sim_t_5>.*

International Search Report from PCT Patent Application No. PCT/US2002/027177 mailed Feb. 14, 2003.

International Search Report from PCT Patent Application No. PCT/US2003/004378 mailed Aug. 13, 2003.

International Search Report from PCT Patent Application No. PCT/US2003/033605 mailed Mar. 29, 2004.

International Search Report from PCT Patent Application No. PCT/US2003/033606 mailed Mar. 29, 2004.

International Search Report from PCT Patent Application No. PCT/US2003/004449 mailed Aug. 13, 2003.

International Search Report from PCT Patent Application No. PCT/US2004/006695 mailed Sep. 8, 2004.

International Search Report from PCT Patent Application No. PCT/US2004/033007 mailed Feb. 9, 2005.

International Search Report from PCT Patent Application No. PCT/US2005/014372 mailed Jul. 28, 2005.

International Search Report from PCT Patent Application No. PCT/US2006/019727 mailed Apr. 19, 2007.

International Search Report from PCT Patent Application No. PCT/US2006/038684 mailed Feb. 14, 2007.

International Search Report from PCT Patent Application No. PCT/US2007/019227 mailed Feb. 20, 2008.

International Search Report from PCT Patent Application No. PCT/US2007/019833 mailed Feb. 20, 2008.

International Search Report from PCT Patent Application No. PCT/US2007/019940 mailed Mar. 14, 2008.

International Search Report from PCT Patent Application No. PCT/US2008/008726 mailed Oct. 16, 2008.

International Search Report from PCT Patent Application No. PCT/US2008/008729 mailed Aug. 18, 2009.

International Search Report from PCT Patent Application No. PCT/US2008/063440 mailed Aug. 1, 2008.

International Search Report from PCT Patent Application No. PCT/US2009/037586 mailed Sep. 28, 2009.

International Search Report from PCT Patent Application No. PCT/US2009/063925 mailed Jan. 12, 2010.

International Search Report from PCT Patent Application No. PCT/US2009/063930 mailed Jan. 12, 2010.

Felsher, et al., "Mucosal apposition in endoscopic suturing"; Gastrointestinal Endoscopy, vol. 58, No. 6, pp. 867-870, (2003).

Stecco, et al., "Trans-oral plication formation and gastric implant placement in a canine model", Stecco Group, San Jose and Barosense, Inc., Redwood City, CA (2004).

Stecco, et al. "Safety of a gastric restrictive implant in a canine model", Stecco group, San Jose amd Barosense, Inc., Redwood City, CA (2004).

The International Search report and Written Opinion for PCT application PCT/US2008/088581, Feb. 26, 2009, 9 pages (2009).

* cited by examiner

GASTRIC SPACE OCCUPIER SYSTEMS AND METHODS OF USE

PRIORITY

This application is a divisional of U.S. patent application Ser. No. 12/270,607, filed Nov. 13, 2008, now abandoned, which claims the benefit of U.S. Provisional Application No. 61/018,405, filed Dec. 31, 2007, both of which are incorporated herein by reference.

TECHNICAL FIELD OF THE INVENTION

The present invention relates generally to the field of implants for inducing weight loss in patients, and specifically to devices and methods for reducing the effective volume of a patient's stomach.

BACKGROUND

Prior art treatments for obesity range from diet and medication to highly invasive surgical procedures. Some of the more successful surgical procedures are the vertical banded gastroplexy or the proximal gastric pouch with a Roux-en-Y anastomosis. However, known complications are present with each of these procedures. More successful and less invasive options are desired.

A less invasive prior art treatment for obesity includes implantation of a gastric space occupier delivered into the stomach via the esophagus. The space occupier is an obstructive device—it prevents overeating by occupying volume within the stomach. Although implantation of a space occupier is less invasive than other surgical procedures, complications do exist. In particular, because space occupiers are typically fluid filled balloons, rupture of balloons can and does occur. A punctured balloon can migrate into the intestines, potentially causing life-threatening intestinal obstruction. Some prior systems attempt to avoid the risk of migration by anchoring space occupiers within the stomach, but these systems tend to nevertheless detach from the stomach wall, resulting in migration. A space occupier which does not pose the threat of obstruction is highly desirable. However, the size of space occupier necessary for weight loss makes a single unit space occupier design difficult.

Additionally, the stomach is a dynamic organ capable of adapting to changes including those associated with positioning of a space occupier. Given the adaptive nature of the stomach, space occupiers do not adequately provide for long term weight loss. It would be advantageous to have a system which could accommodate such adaptations, thus allowing for long term weight loss.

The present application describes space occupier designs that minimize risk of obstruction, as well as methods for using the designs in a manner that addresses stomach adaptations and/or changes to the amount of volume consumption needed for a given patient.

BRIEF DESCRIPTION OF THE DRAWINGS

FIGS. 5 and 6 are cross-section views of the space occupier of FIG. 4A, in which FIG. 5 shows the space occupier in an insertion position and FIG. 6 shows locking of the space occupier into an expanded position;

DETAILED DESCRIPTION

The disclosed embodiments address the shortcomings of prior art space occupier technologies. In preferred modes of use, the disclosed systems utilize a number of space occupiers positioned in the stomach. Such an arrangement provides sufficient stomach volume consumption to induce weight loss, but enables use of space occupiers that are proportioned to minimize the threat of obstruction even if they should migrate into the intestine. In general, numerous small volume space occupiers are placed in the stomach such that the total volume equals or exceeds the single volume of known space occupiers. However, each individual space occupier is proportioned so that it will pass without obstruction if it moves into the intestine. The devices are capable of being inserted trans orally, but once in the stomach the space occupiers are expanded or otherwise changed into a shape or size which prevents migration into the intestinal tract. Because they are smaller than known space occupiers, additional individual units may be introduced into the stomach to increase the rate of weight loss or to accommodate changes in the stomach size.

Figure 1:
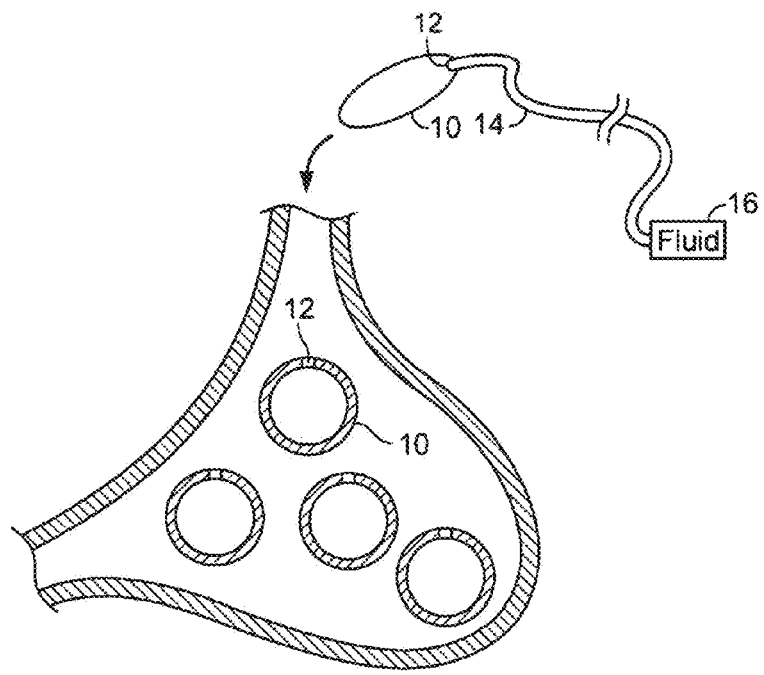
FIG. 1 schematically shows a cross-section view of a stomach, with a plurality of space occupiers positioned within the stomach.

The disclosed embodiments are preferably formed using materials such as silicone that are capable of withstanding the acidic environment of the stomach, and they are sufficiently soft and appropriately shaped to be atraumatic to the tissue of the stomach. Numerous embodiments are conceivable, a few of which are shown herein. FIG. 1 shows a first embodiment of a space occupier system in which a number of fluid filled space occupiers 10 are transorally passed into the stomach. Ideally the volume of each individual balloon is between 50 200 cc, but preferably between 75 and 125 cc. By placing two or more balloons of this size into the stomach, adequate stomach volume is taken up such that weight loss occurs. In some embodiments, the collective volume occupied by the collection of space occupiers can be 300 cc or more (e.g. in a range between approximately 300 cc and 700 cc).

Each space occupier has a deflated or compressed position allowing its insertion into the stomach via the esophagus as shown. The system may be provided with instruments that facilitate implantation, such as an overtube positionable in the esophagus (through which the space occupiers are passed), and instruments for advancing the space occupiers through the overtube or directly through the esophagus. Such instruments might include push tools that push the space occupiers through the esophagus or overtube, or graspers or alternative instruments that can be used to carry space occupiers through the esophagus or overtube.

Figure 2:
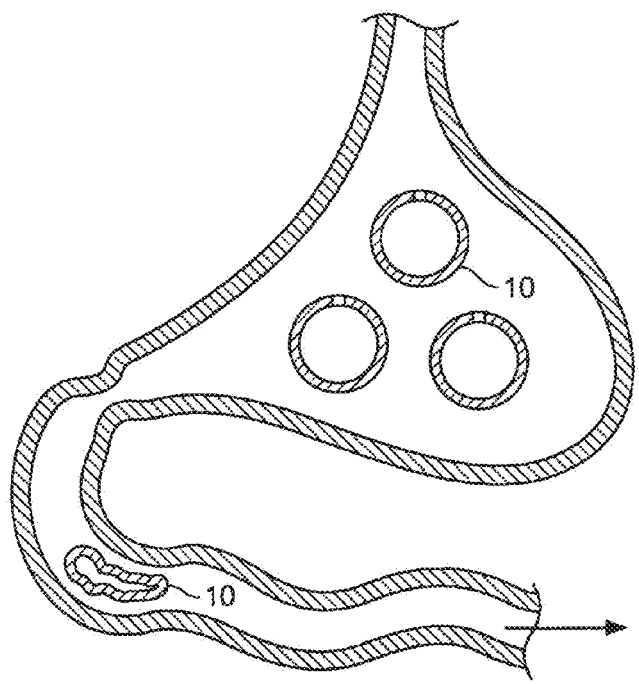
FIG. 2 is similar to FIG. 1, and shows one of the space occupiers deflated and passing through the intestine.

Once a space occupier is positioned in the stomach, fluid (e.g. liquid, gas, gel) is introduced into the space occupier through a valve 12. In one example, an inflation tube 14 is coupled to the valve prior to introduction of the space occupier into the stomach, and is subsequently detached from the space occupier following inflation. Inflation tube is coupled to a fluid source 16 such as a fluid-filled syringe or canister. The space occupiers are shown as spherical but may be any shape that will resist passage into the digestive tract when filled with fluid, but that will readily pass into the digestive tract, as shown in FIG. 2, when the fluid is released such as through rupture.

The number of space occupier units implanted at any given time is selected to give a target stomach volume consumption selected to yield the desired weight loss results. Additional units may be added, or some units removed, during the course of weight loss treatment to increase or decrease the total volume consumption and the corresponding rate of weight loss and/or to respond to adaptive changes in the stomach's volume.

Figure 3:
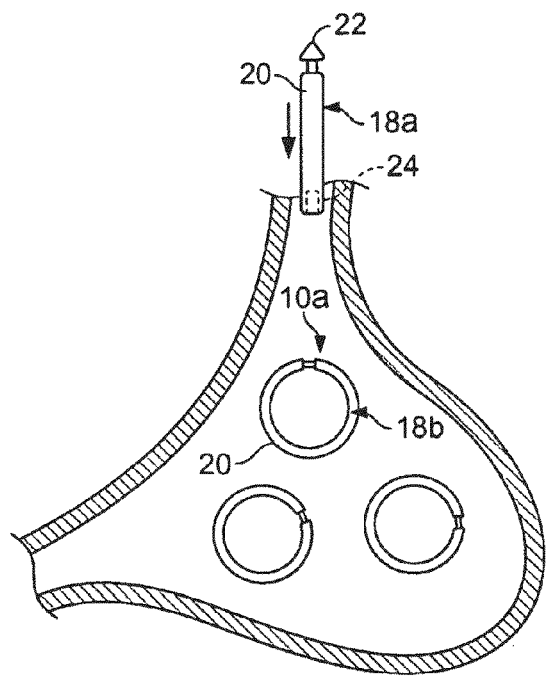
FIG. 3 is similar to FIG. 1 and illustrates use of a second type of space occupier.

FIG. 3 illustrates use of an alternate form of space occupier 10*a* that need not be inflatable but that is positioned in a first streamlined shape 18*a* for insertion into the stomach and is then manipulated into a different, less streamlined shape 18*b* that will resist passage into the digestive tract. In this embodiment, the space occupier 10*a* is an elongate band 20 having a locking feature that joins the ends of the band to form a cylindrical element or oval shaped element. In one configuration, the locking feature includes a tab 22 on one end and a receptacle 24 on the other end for receiving the tab in locking engagement.

Figure 4A:
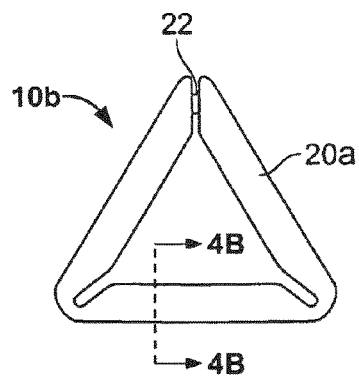
FIG. 4A is a side elevation view of an alternative to the space occupier of FIG. 3.
Figure 4B:
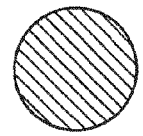
FIG. 4B is a cross-section view taken along the plane designated 4B-4B in FIG. 4A.

The FIG. 3 embodiment may be constructed to form a wide variety of alternate shapes beyond a cylindrical or oval shape. For example, FIG. 4A shows a modification to the FIG. 3 embodiment in which the ends of band 20*a* are coupled together to form a space occupier 10*b* having a triangular shape. Band 20*a* may have a circular cross-section as shown in FIG. 4B to give the space occupier a smooth exterior surface. Suitable diameters for the band range from 0.25-1 inches, or more preferably 0.5-0.75 inches.

Figure 5:
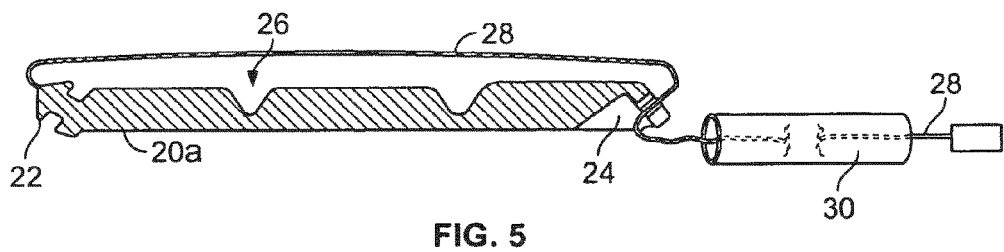

As shown in FIG. 5, the band 20*a* may formed to include predetermined bend locations 26 formed using, for example, weakened or thinned regions of band material. In the illustrated embodiment, bend locations are formed by forming v-shaped hinges into the band material.

For implantation, the band is positioned in its linear/streamlined configuration and introduced into the stomach as shown in FIG. 3. Overtubes, pushers, graspers etc may be used to facilitate instruction of the band into the stomach as indicated in connection with the FIG. 1 embodiment.

Figure 6:
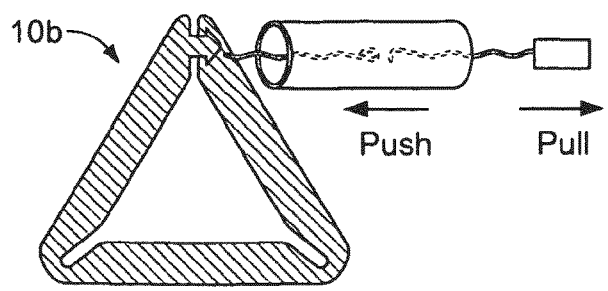

Once the band has been passed into the stomach, the ends of the band are brought together to form the band into a shape that will be unable to pass into the intestinal tract (such a shape may be referred to herein as a "non-passable shape"). Various tools or actuators may be used for this purpose. In one example shown in FIG. 5, a tether 28 is coupled to tab 22 and threaded through the receptacle 24 and also through a pusher tube 30. To couple the ends of the band 20*a*, tether 28 is withdrawn while pusher tube 30 is pushed against the band 20*a* as shown in FIG. 6, causing the tab 22 to pass into and become engaged in the receptacle 24. The tether 28 and pusher 30 are proportioned such that their proximal ends may be manipulated in this manner from outside the body. If the tab should become disengaged, the band will return to the streamlined shape and thus will be able to pass through the intestinal tract without harm to the patient.

As with the FIG. 1 embodiment, multiple units of the space occupier 10*a*, 10*b* are preferably used at one time to achieve a desired collective volume consumption within the stomach, such as that described in connection with the FIG. 1 embodiment. The number of units placed in the stomach may be decreased or increased as needed to achieve the target weight loss.

Figure 7:
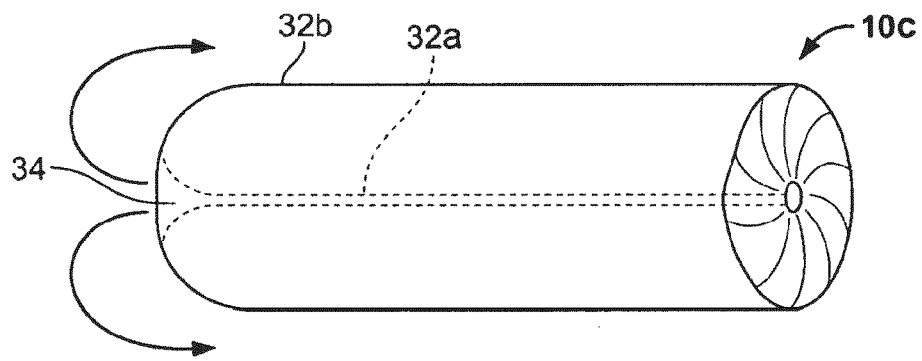
FIG. 7 is a side elevation view of yet another embodiment of a space occupier.

FIG. 7 illustrates yet another embodiment of a gastric space occupier 10*c* having a shape that inhibits passage of the space occupier into the digestive tract. Space occupier 10*c* is a tubular balloon. The balloon has inner and outer walls 32*a*, 32*b*, and a fluid between the inner and outer walls. A lumen 34 extends longitudinally through the tubular balloon.

Figure 8:
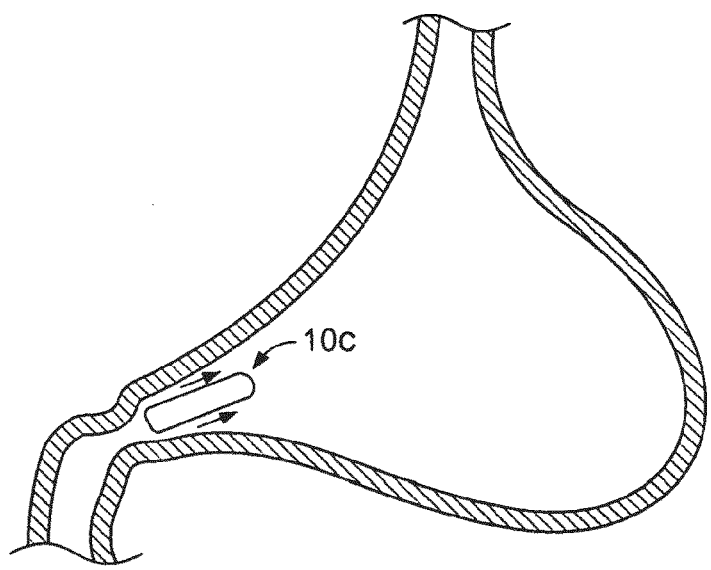
FIG. 8 is similar to FIG. 1, and illustrates the ability of the space occupier of FIG. 7 to shoot upwardly when it migrates into contact with the pyloric sphincter.

The construction of the space occupier 10*c* is similar to that of a children's' toy known as a "water snake". In particular, the space occupier is configured such that squeezing the outer surface at one end will "squirt" the space occupier away from the point of compression by causing the layer of wall lining the lumen 34 to roll to the outside of the 25 balloon while the layer of wall lining the outer surface of the balloon rolls into the lumen as indicated by arrows in FIG. 7. This feature aids in preventing the device from passing into the digestive tract. In particular, should the device begin to migrate into the digestive tract, its distal-facing end will be compressed or squeezed as it descends into the pyloric antrum and/or abuts the pyloric sphincter. In response to this compression, the device walls will propel the device away from the pyloric sphincter as shown in FIG. 8.

Figure 9A:
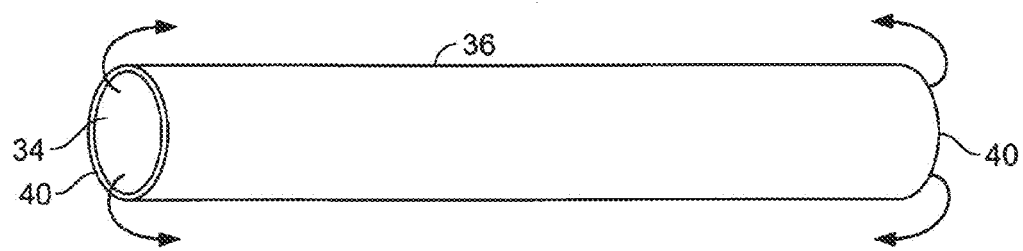
FIGS. 9A and 9B illustrate steps in the manufacture of the space occupier of FIG. 7.
Figure 9B:
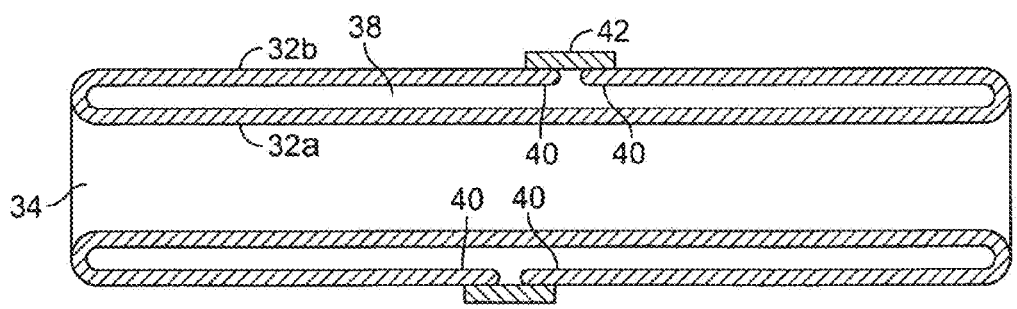

FIGS. 9A and 9B illustrate steps of manufacturing the space occupier 10*c*. Referring to FIG. 9A, a tube 36 having lumen 34 is provided. Tube 36 may have a uniform diameter, and it can be formed of a thin-walled extrusion of silicone, urethane, or other suitable material. The ends 40 of the tube are everted and brought together on the exterior of the tube, thus giving the tube a double-layer wall. Fluid is introduced into the space 38 between the layers 32*a*, 32*b* of the wall. A seal 42 is applied to seal the ends 40 together and to seal the fluid within the space 38. Seal 42 may include a valve, allowing the fluid to be introduced in situ as described with respect to the FIG. 1 embodiment. Alternatively, the seal may be provided without a valve. This embodiment may be used as a single unit, or multiple units may be implanted in the stomach.

As with previously described embodiments, obesity using the space occupier 10*c* may involve placing a single space occupier or multiple space occupiers within the stomach to achieve a desired collective volume consumption within the stomach, such as that described in connection with the FIG. 1 embodiment. As with the previous embodiments, the overall and/or rate of weight loss is monitored, and the number of units may be decreased or increased as needed to achieve the target weight loss or rate of weight loss. The space occupiers 10*c* may be passed through an endogastric overtube or introduced into the stomach by some other means.

The disclosed space occupiers and associated systems may be provided with instructions for use instructing the user to utilize the space occupiers according to the various steps described herein.

It should be recognized that a number of variations of the above-identified embodiments will be obvious to one of ordinary skill in the art in view of the foregoing description. Moreover, various features of the disclosed embodiments may be combined in a variety of ways. Accordingly, the invention is not to be limited by those specific embodiments and methods of the present invention shown and described herein. Rather, the scope of the invention is to be defined by the following claims and their equivalents.

Any and all prior patents and applications referred to herein, including for purposes of priority, are fully incorporated by reference.

We claim:

1. A method of treating obesity in a patient, comprising:
placing a tubular balloon into a stomach, the tubular balloon including a tubular wall comprising an outer tubular layer and an inner tubular layer disposed within the outer tubular layer, and a space between the inner and outer tubular layers, wherein the tubular balloon defines an elongate lumen therethrough, and wherein, in response to a radially inward pressure against an outer surface of the tubular balloon, a portion of the inner tubular layer moves from within the elongate lumen to an external location on the tubular balloon; and
filling the space between the inner and outer tubular layers with a fluid such that the fluid is contained within the tubular wall.

2. The method of claim 1, wherein the method further includes:
in the event the tubular balloon advances from the stomach into contact with walls of a lumen of the stomach or intestine that is sufficiently narrow to impart radially inward pressure against the tubular balloon, allowing the inner and outer tubular layers to slide relative to one another in the opposite directions, causing the tubular balloon to move proximally within the stomach.

3. The method of claim 1, wherein filling the space includes filling the space prior to placing the tubular balloon into the stomach.

4. The method of claim 1, wherein filling the space includes filling the space after placing the tubular balloon into the stomach.

5. The method of claim 1, wherein the method includes placing a plurality of the tubular balloons into the stomach.

6. The method of claim 5, further including monitoring a rate of weight loss by the patient, and removing at least one tubular balloons from the stomach to decrease the rate of weight loss.

7. The method of claim 1, further including monitoring a rate of weight loss by the patient, and placing additional tubular balloons into the stomach to increase the rate of weight loss.

8. The method of claim 1, wherein the tubular balloon reduces the effective volume of the stomach by an amount sufficient to cause the patient to lose weight.

9. A method of treating obesity in a patient using a gastric implant, comprising:
introducing a plurality of gastric balloons within the stomach, each gastric balloon having a volume in the range of approximately 50-200 cc, wherein the plurality of gastric balloons reduce the effective volume of the stomach by an amount sufficient to cause the patient to lose weight, and wherein each gastric balloon comprises:
a tubular wall comprising an outer tubular layer and an inner tubular layer disposed within the outer tubular layer, the inner and outer tubular layers having a space therebetween, the wall defining an elongate lumen extending through the gastric balloon; and
a fluid in the space between the inner and outer tubular layers, wherein, in response to radially inward pressure against an outer surface of the gastric balloon, a portion of the inner tubular layer moves from within the elongate lumen to an external location on the gastric balloon.

10. The method of claim 9, wherein each gastric balloon has a volume in the range of approximately 75-125 cc.

11. The method of claim 9, further including monitoring a rate of weight loss by the patent, and removing at least one gastric balloon from the stomach to decrease the rate of weight loss.

12. The method of claim 9, further including monitoring a rate of weight loss by the patent, and placing additional gastric balloons into the stomach to increase the rate of weight loss.

13. The method of claim 9, wherein the gastric balloons collectively occupy at least approximately 300 cc of stomach volume.

* * * * *